United States Patent
Weber et al.

[11] Patent Number: 5,470,990
[45] Date of Patent: Nov. 28, 1995

[54] SULFONATION OF BENZOFURANYLBIPHENYLS

[75] Inventors: Kurt Weber, Basel; Hans R. Meyer, Binningen, both of Switzerland; Jürgen Kaschig, Freiburg, Germany; Claude Eckhardt, Riedisheim, France

[73] Assignee: Ciba-Geigy Corporation, Ardsley, N.Y.

[21] Appl. No.: 325,010

[22] Filed: Oct. 18, 1994

Related U.S. Application Data

[63] Continuation of Ser. No. 47,586, Apr. 13, 1993, abandoned, which is a continuation-in-part of Ser. No. 789,392, Nov. 7, 1991, abandoned, which is a continuation of Ser. No. 360,576, Jun. 1, 1989, abandoned.

[30] Foreign Application Priority Data

Jun. 2, 1988 [CH] Switzerland ............... 2090/88

[51] Int. Cl.$^6$ ................. C07D 307/82
[52] U.S. Cl. ................. 549/466; 549/469
[58] Field of Search ................. 549/466

[56] References Cited

U.S. PATENT DOCUMENTS

| | | | |
|---|---|---|---|
| 3,859,350 | 1/1975 | Sohm | 260/346 |
| 4,133,953 | 1/1979 | Schinzel | 542/454 |
| 4,670,882 | 6/1987 | Telle | 372/53 |

FOREIGN PATENT DOCUMENTS 50-40627  4/1975  Japan.

OTHER PUBLICATIONS

Chem. Abstract, 116988, Japan Apr. 1975.

*Primary Examiner*—Bernard Dentz
*Attorney, Agent, or Firm*—Kevin T. Mansfield

[57] ABSTRACT

Novel benzofuranylbiphenyl compounds of the formula

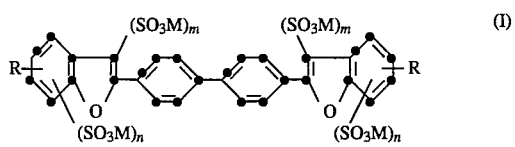

which are unsubstituted or polysubstituted by radicals R=hydrogen, $C_1$–$C_4$alkyl, $C_1$–$C_4$alkoxy, halogen, phenoxy and benzyloxy and in which M is hydrogen and/or one equivalent of a non-chromophoric cation and n is the number zero, 1 or 2 and m is the number zero or 1, subject to the condition that n and m are not both zero, and the preparation and use thereof as fluorescent brighteners, for example for textiles and paper. The novel benzofuranylbiphenyl compounds are distinguished by their very good stability associated with excellent whitening properties.

6 Claims, No Drawings

SULFONATION OF BENZOFURANYLBIPHENYLS

CROSS-REFERENCE TO RELATED APPLICATIONS

This is a continuation of Ser. No. 08/047,586, filed Apr. 13, 1993, abandoned, which is a continuation-in-part of Ser. No. 07/789,392, filed Nov. 7, 1991, now abandoned, which is a continuation of Ser. No. 07/360,576, filed Jun. 1, 1989, now abandoned.

The present invention relates to sulfonated benzofuranylbiphenyl compounds and to their preparation and their use as fluorescent whitening agents.

Mixtures of sulfonated benzofuranylbiphenyl compounds of an undefined composition and structure and their use as optical brighteners have been known for a long time (DE-A 2,238,734, DE-A 2,238,628, DE-A 2,361,338 and DE-A 2,843,850). Hitherto, however, it has not been possible to prepare individual compounds having a single structure.

It has now been found, surprisingly, that sulfonated benzofuranylbiphenyl compounds of a definite structure can be prepared selectively by specific processes and that these substantially pure individual compounds have outstanding whitening properties, for example for whitening textiles and paper.

The application therefore relates to substantially pure benzofuranylbiphenyl compounds of the formula (I)

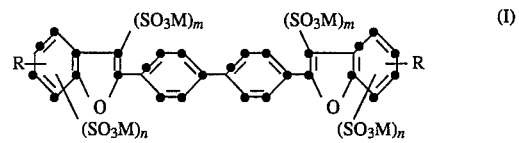

which are unsubstituted or are polysubstituted by radicals R=hydrogen, $C_1$–$C_4$alkyl, $C_1$–$C_4$alkoxy, halogen, phenoxy and benzyloxy and in which M is hydrogen and/or one equivalent of a non-chromophoric cation and n is the number zero, 1 or 2 and m is the number zero or 1, subject to the condition that n and m are not both zero.

As a non-chromophoric cation, M is, for example, an alkaline earth metal, such as magnesium and calcium, but is preferably an alkali metal, such as lithium, sodium and potassium or substituted or unsubstituted ammonium, such as ammonium, mono-, di- or tri-ethanolammonium, mono-, di- or tri-propanolammonium or trimethylammonium or tetramethylammonium.

Preferred compounds are those of the formula (II) and (V)

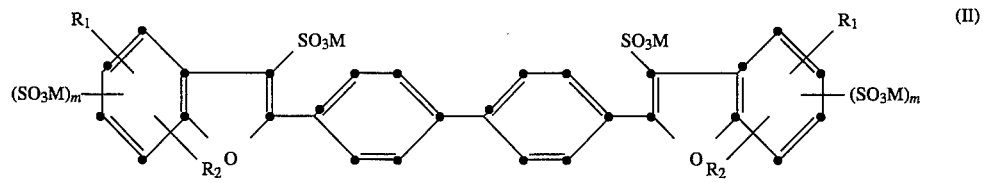

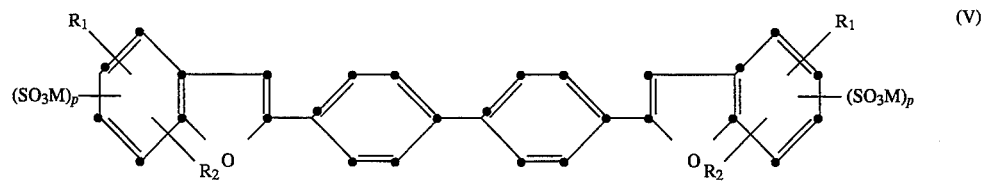

in which $R_1$ is hydrogen, $C_1$–$C_4$alkyl, chlorine, $C_1$–$C_4$alkoxy, phenoxy or benzyloxy, $R_2$ is hydrogen, $C_1$–$C_4$alkyl, chlorine or $C_1$–$C_4$alkoxy, M is hydrogen and/or one equivalent of a non-chromophoric cation and m is the number zero or 1 and p is the number 1 or 2, and, in particular, compounds of the formula (III), (VI) and (VIII)

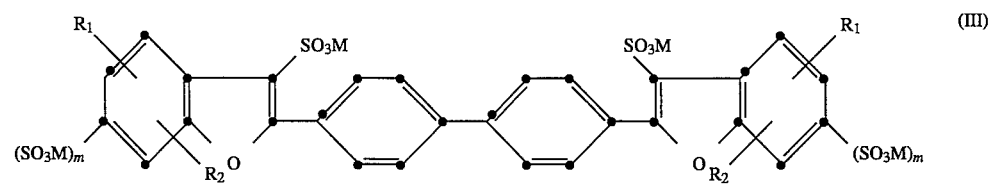

-continued

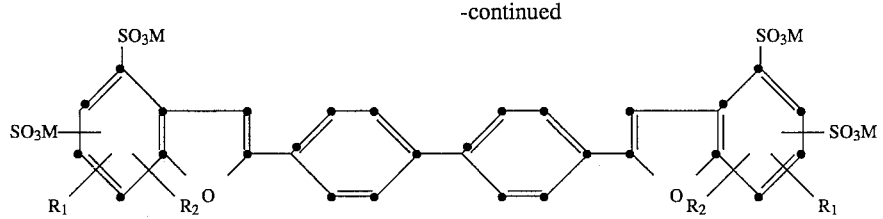

(VI)

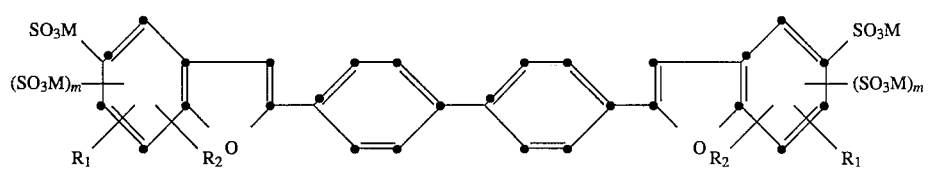

(VIII)

in which $R_1$, $R_2$, M and m are as defined above.

Compounds of particular interest are, however, those of the formula (IV), (VII) and (IX)

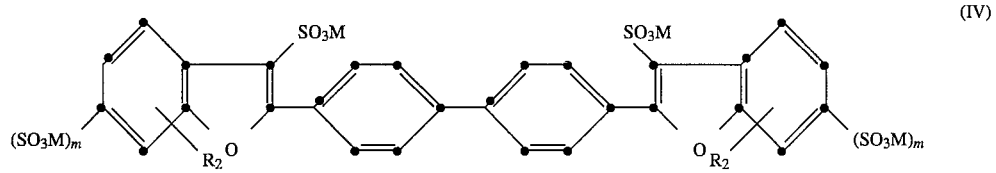

(IV)

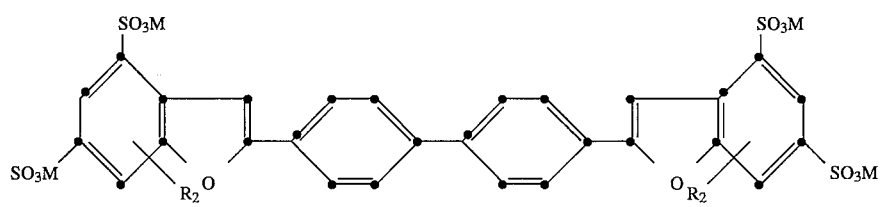

(VII)

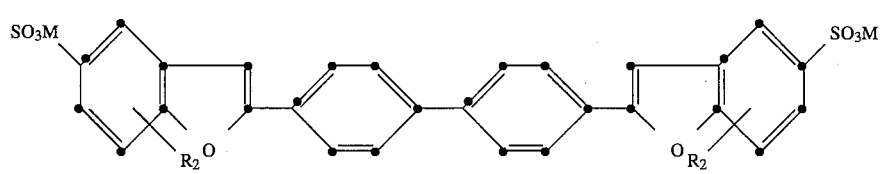

(IX)

in which $R_2$, M and m are as defined above. $R_2$ is preferably hydrogen.

This application also relates to processes for the preparation of the compounds of the formula (I), which comprise a) reacting one mole of the compound of the formula (X)

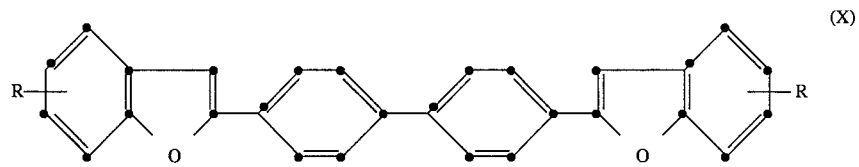

(X)

which is unsubstituted or polysubstituted by radicals R=hydrogen, $C_1$–$C_4$alkyl, $C_1$–$C_4$alkoxy, halogen, phenoxy and benzyloxy, with at least stoichiometric amounts of an $SO_3$/base complex in an inert organic solvent, at temperatures from 20° C. up to the boiling point of the solvent used, or b) reacting one mole of the compound of the formula (X) with at least stoichiometric amounts of chlorosulfonic acid in an inert organic solvent, at temperatures from 0° to 40° C., or c) heating the compound of the formula (X) with concentrated sulfuric acid at temperatures from 40° to 80°

C., or d) etherifying one mole of 4,4'-bis-(halogenomethyl)-biphenyl with at least 2 moles of salicylaldehyde or anils thereof of the formula (XI) or (XII)

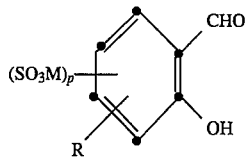
(XI)

or

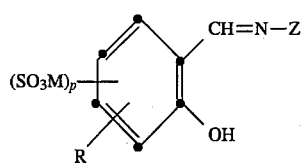
(XII)

which are unsubstituted or polysubstituted by radicals R=hydrogen, $C_1$–$C_4$alkyl, $C_1$–$C_4$alkoxy, halogen, phenoxy and benzyloxy and in which M is hydrogen and/or one equivalent of a non-chromophoric cation, p is the number 1 or 2 and Z is phenyl or chlorophenyl, and cyclizing by means of bases the resulting bisbenzyl ethers of the formula (XIII) or (XIV)

Specifically, the compounds of the formula (II), (III) and (IV) and, in particular, the compounds of the formula (II), (III) and (IV) in which m is zero, are prepared by process a).

$SO_3$/base complexes are to be understood as meaning addition compounds of $SO_3$ with organic bases, for example dioxane, preferably nitrogen-containing bases, for example triethylamine, N-ethyldiisopropylamine, dimethylformamide (DMF) and especially pyridine. The stability of these addition compounds is a decisive factor in this reaction for the degree of sulfonation. Thus, for example, if 2 to 6, in particular 3 to 5, moles of $SO_3$/pyridine complex (based on the $SO_3$ content) are used per mole of the compound of the formula (X), compounds of the formula (II)–(IV) in which m is zero are prepared, and, if 2 to 6, in particular 3 to 5, moles of $SO_3$/DMF (based on the $SO_3$ content) are used per mole of the compound of the formula (X), compounds of the formula (II)–(IV) in which m is 1 are prepared. $SO_3$/base complexes are known and can be prepared by known methods (E. E. Gilbert, E. P. Jones, Ind. Enging. Chem. 49, No. 9, Part II, pages 1553 et seq. (1957); Beilstein 20, III/IV, 2232).

It is preferable, however, to prepare the compounds of the formula (III) and (IV) in which m is 1 by process b). In this process one mole of the compound of the formula (X), in particular, is reacted with 2 to 20, in particular 6 to 14, moles of chlorosulfonic acid at temperatures from 0° to 40° C., in particular 5° to 25° C., in an inert organic solvent, for example saturated aliphatic hydrocarbons, such as gasoline, petroleum ether and ligroin, halogenated, aliphatic hydrocarbons, such as chloroform, carbon tetrachloride, dichloroethane, trichloroethane, tetrachloroethane, dichloropropane, trichloropropane, dichlorodifluoromethane and dichlorotetrafluoroethane, chlorobenzenes, such as mono-, di- and tri-chlorobenzene, nitrobenzenes, such as nitroben-

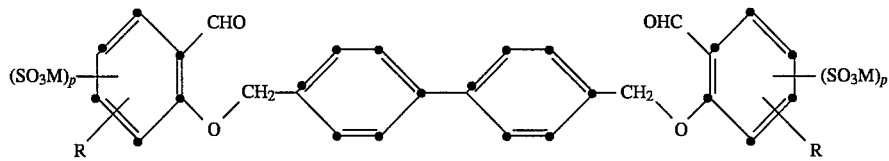
(XIII)

or

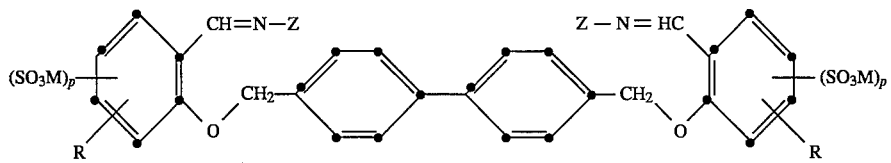
(XIV)

The starting compounds of the formula (X), (XI) and (XII) are known and can be prepared by known methods. The intermediates of the formula (XIII) and (XIV) are novel and can be isolated. However, it is advantageous to carry out the process d) as a one-pot process without isolating the intermediates (XIII) and (XIV).

zene and nitrotoluene, and bicyclic hydrocarbons, such as cyclohexane, methylcyclohexane and decalin.

These solvents are also used in process a).

The compounds of the formula (V) and, in particular, the compounds of the formula (VI) and (VII) are prepared by process c). In this process one part of the compound of the formula (X), in particular, is heated with 10 to 100, preferably 20 to 80 and especially 30 to 60, parts of 90 to 100% sulfuric acid, with stirring, at temperatures from 40° to 80° C., preferably 55° to 70° C.

The compounds of the formula (V) and, in particular, the compounds of the formula (VIII) and (IX) are similarly prepared by process d).

The etherification is carried out at temperatures from 60° to 140° C., in particular 100° to 120° C., in a known manner by means of one equivalent of a base, such as a tertiary amine or a base mentioned in the cyclization below, or by employing the compounds of the formula (XI) or (XII) already converted into the phenate of this base. The reaction is carried out in a polar, aprotic solvent or solvent mixture, for example dimethylformamide, N-methylpyrrolidone, hexamethylphosphoric triamide, tetramethylurea or, preferably, dimethyl sulfoxide.

The cyclization is similarly carried out in a polar, aprotic solvent, preferably in the same solvent in which the etherification is also carried out, at slightly higher temperatures compared with the etherification and in the presence of a base, for example quaternary ammonium bases, alkaline earth metal hydroxides, alkali metal amides, alkali metal hydrides, alkali metal carbonates and, preferably, alkali metal alcoholates, such as potassium t-butylate and sodium methylate, and also, in particular, alkali metal hydroxides, such as sodium hydroxide, potassium hydroxide and lithium hydroxide. The basic condensation agents are employed in at least stoichiometric amounts, preferably in excess. It is advantageous to carry out the reaction with the exclusion of atmospheric oxygen and under an inert gas atmosphere.

The benzofuranylbiphenyl compounds according to the invention are used for the fluorescent whitening of textiles, for example fabrics containing cellulose and/or polyamide, and also paper. The benzofuranylbiphenyl compounds according to the invention are preferably incorporated into bleaching agents containing, for example, hypochlorite or, in particular, into detergents.

The benzofuranylbiphenyl compounds according to the invention are distinguished by their very good stability, asssociated with excellent whitening properties.

The following examples illustrate the invention; parts and percentages are by weight.

EXAMPLE 1

11.8 g (0.03 mol) of the Compound of the Formula

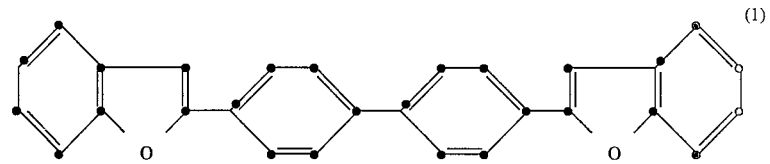

are suspended by stirring in 250 ml of tetrachloroethane. 35 g (0.3 mol) of chlorosulfonic acid are then added dropwise at 5° C. in the course of 30 minutes. The suspension is stirred for 1 hour at 5° C. and for 3 hours at room temperature. After being filtered off with suction the product is washed with chloroform, suspended in 200 ml of water, the pH of which is adjusted to 9 with sodium hydroxide solution, 200 ml of methanol are added, the mixture is heated to the boil and filtered while hot, the filtrate is cooled to −5° C. and the product which has crystallized out is filtered off with suction, recrystallized from a mixture of 100 ml of water and 100 ml of ethanol and dried in vacuo. This gives 8.3 g of a mixture consisting of the sulfonation product of the formula

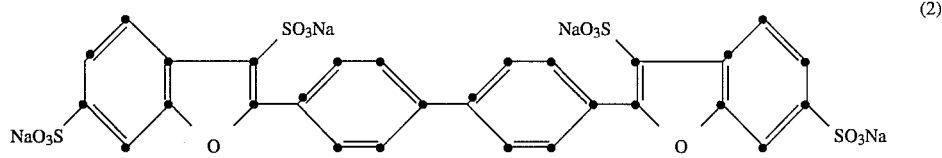

and sodium sulfate.

| HPLC analysis: | | |
| --- | --- | --- |
| Component: | RT: | Area/% |
| 1 | 7.39 | 13907078/100% |

EXAMPLE 2

11.8 g (0.03 mol) of the compound of the formula (1), together with 21 g (0.12 mol of $SO_3$) of sulfur trioxide/pyridine complex (containing approx. 45% of $SO_3$), in 50 ml of nitrobenzene are heated at 125° C. for 15 hours, with stirring. The nitrobenzene is then removed by means of steam, the resulting suspension is rendered alkaline with sodium hydroxide solution and the product is filtered off with suction and recrystallized from a mixture of 150 ml of water and 150 ml of ethanol. This gives 4.7 g of the compound of the formula

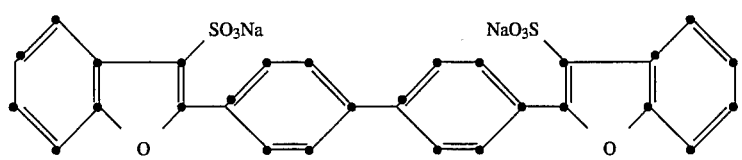

(3)

| HPLC analysis: | | |
|---|---|---|
| Component: | RT: | Area/% |
| 1 | 8.43 | 6697083/98% |
| 2 | 12.85 | 137387/2% |

EXAMPLE 3

10 g of the compound of the formula (1) in 200 ml (368 g) of sulfuric acid (strength: 96%) are heated at 60°–65° C. for 7 hours, with stirring. The reaction mixture is then cooled to room temperature, poured into 100 ml of water and neutralized with sodium hydroxide solution and the precipitated product is filtered off. The filtrate is evaporated to dryness and the residue is dried at 100° C. in vacuo and extracted with methanol for 16 hours in a Soxhlet extractor. The solution is evaporated to dryness, the residue is dissolved in 150 ml of water, the cloudy solution is clarified by filtration and 450 ml of ethanol are added to it. The precipitated product is filtered off with suction and recrystallized first from a mixture of 25 ml of water and 25 ml of ethanol and then from 40 ml of water and 240 ml of ethanol and is dried at 100° C. in vacuo. This gives 3 g of a mixture consisting of the compound of the formula

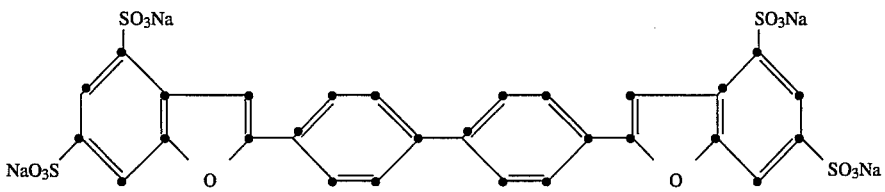

(4)

and sodium sulfate.

| HPLC analysis: | | |
|---|---|---|
| Component: | RT: | Area/% |
| 1 | 6.32 | 217152/8.9% |
| 2 | 7.35 | 2233809/91.1% |

EXAMPLE 4

27.1 g (0.11 mol) of disodium salicylaldehyde-5-sulfonate are stirred in 200 ml of dimethyl sulfoxide at 100° C. A solution, preheated to 60°, of 13.4 g (0.05 mol) of 94% 4,4'-bis-(chloromethyl)-biphenyl is added dropwise to the resulting suspension in the course of one hour. The salicylaldehyde derivative goes into solution meanwhile and a little bisbenzyl ether of the formula is precipitated. If it is desired to isolate the ether completely, the solvent is removed by vacuum distillation, the residue is stirred with 250 ml of water and the product is filtered off and washed with water, methanol and acetone. The prior isolation of the compound of the formula (5) is not necessary for the subsequent cyclization reaction.

| HPLC analysis of compound (5): | | |
|---|---|---|
| Component: | RT: | Area/% |
| 1 | 5.55 | 369855/100% |

8.2 g (0.2 mol) of finely powdered sodium hydroxide are introduced, with nitrogen blanketing, into the hot reaction mixture previously described and stirring is continued for one hour at 100° C. and for 16 hours at 120° C. In the course of this the end product is partially precipitated. Approx. 180 ml of solvent are removed by vacuum distillation at 120° C., the residue is allowed to cool and the precipitate is filtered off with suction. After repeated washing with dimethyl sulfoxide, methanol and water and drying in vacuo, 13.1 g of the compound of the formula

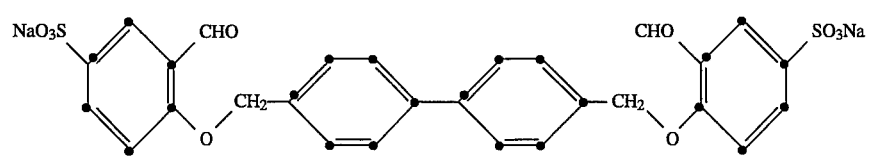

(5)

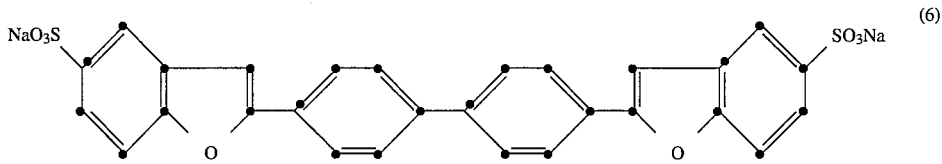

are obtained.

| HPLC analysis: | | |
|---|---|---|
| Component: | RT: | Area/% |
| 1 | 5.21 | 395453/4.166% |
| 2 | 6.53 | 547816/5.772% |
| 3 | 6.84 | 7606472/80.140% |
| 4 | 7.59 | 184748/1.946% |
| 5 | 10.25 | 186221/1.962% |
| 6 | 10.54 | 104556/1.102% |
| 7 | 11.44 | 466210/4.912% |

| HPLC analysis: | | |
|---|---|---|
| Component: | RT: | Area/% |
| 1 | 6.56 | 205129/3.250% |
| 2 | 6.88 | 4886737/77.413% |
| 3 | 7.96 | 875655/13.872% |
| 4 | 9.90 | 299601/4.746% |
| 5 | 11.51 | 45426/0.720% |

EXAMPLE 5

A suspension of 11.8 g of the compound of the formula (6) in 240 ml of chlorobenzene, 10 ml of thionyl chloride and 0.3 ml of dimethylformamide is stirred for 2 hours at reflux temperature. A little more thionyl chloride and dimethylformamide are added in order to complete the reaction and stirring is continued at reflux temperature. The resulting cloudy solution is clarified by hot filtration, concentrated greatly and cooled. The precipitated product is filtered off with suction, washed with chlorobenzene and dried. This gives the disulfochloride of the formula If excess concentrated hydrochloric acid is added to such a solution at 95° C., with stirring, the monotriethanolamine salt of the formula

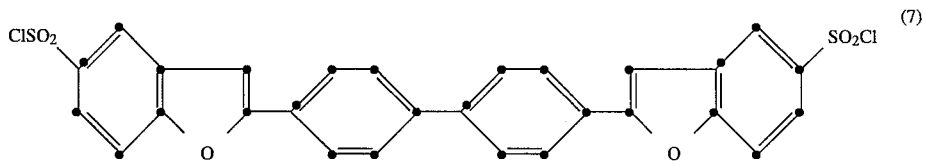

and this is recrystallized from chlorobenzene.

A suspension of 3.7 g of the sulfochloride of the formula (7) in 15 g of triethanolamine and 3 g of water is stirred at 150° for one hour. The excess solvent is substantially removed in vacuo at 120°–150° C., and 50 ml of isopropanol are added to the viscous residue. The precipitated product is filtered off with suction, washed repeatedly with isopropanol and taken up in approx. 40 ml of water. The cloudy solution is clarified by filtration with 0.2 g of active charcoal through a pressure filter. This gives an aqueous solution of the bistriethanolamine salt of the formula

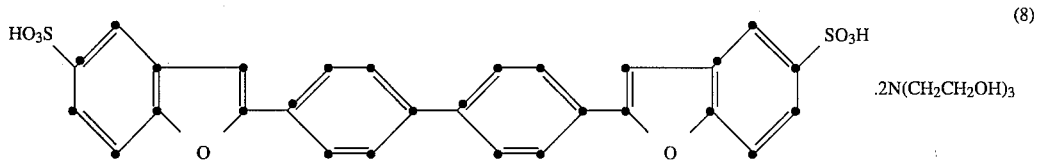

which still contains triethanolamine hydrochloride.

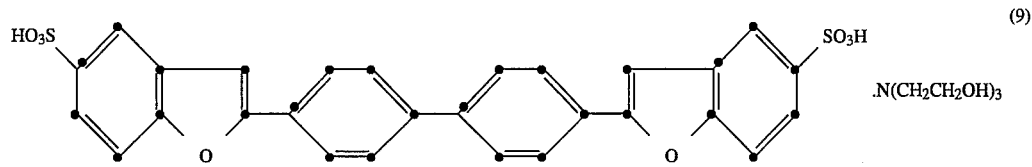

is precipitated. This salt is filtered off with suction, washed with dilute hydrochloric acid and a little water and dried.

EXAMPLES 6 to 10

Using the procedure of Example 2, a compound of the formula:

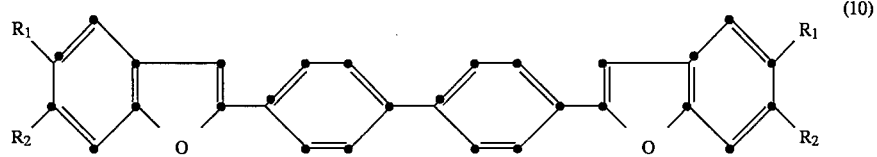

is sulfonated to produce a corresponding compound having the formula:

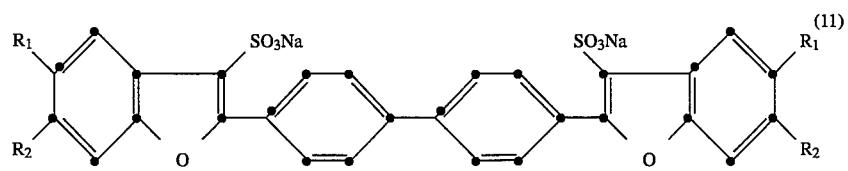

| | Compound | | | HPLC data | | | |
|---|---|---|---|---|---|---|---|
| Example | Number | $R_1$ | $R_2$ | Compound No. | RT | Area | % |
| 6 | 12 | $C(CH_3)_3$ | H | 1 | 11.37 | 4937621 | 100 |
| 7 | 13 | $CH_3$ | H | 1 | 8.67 | 216665 | 4.7 |
| | | | | 2 | 9.13 | 4381512 | 95.3 |
| 8 | 14 | H | $CH_3$ | 1 | 8.74 | 79815 | 3.4 |
| | | | | 2 | 9.19 | 2301530 | 96.6 |
| 9 | 15 | $CH(CH_3)_2$ | H | 1 | 10.89 | 397349 | 100 |
| 10 | 16 | $CH_2CH_3$ | H | 1 | 9.72 | 49754 | 2.3 |
| | | | | 2 | 10.14 | 2121433 | 97.7 |

The starting materials of formula (10) are either known compounds or they can be made by known processes.

EXAMPLE 11

A piece of polyamide 66 (nylon woven tricot) is heated from 40° C. to 98° C. in the course of 30 minutes at a liquor ratio of 1:20 in soft water containing 0.1% of the compound of the formula (3) (percentage by weight based on the textile material) and 3 g/l of stabilized hydrosulfite and 1 ml/l of 80% acetic acid, and is then treated at 98° C. for 30 minutes, cooled again to 40° C. in the course of 15 minutes, rinsed under cold conditions and dried at 60° C. in a drying cabinet.

A high and brilliant degree of whiteness results. When exposed to light in a ®Xenotest apparatus by the customary standard method, this white effect displays an excellent fastness to light.

EXAMPLE 12

1 g of the compound of the formula (3) is dissolved in 1 l of soft water containing 2 g/l of polyphosphate and 5 ml of 80% acetic acid. A piece of polyamide 6 (®Perlon woven tricot) is padded under cold conditions with this liquor, at a liquor pick-up of 110%, and is then thermofixed for 40 seconds at 190° C. After this treatment the textile material has a high degree of whiteness with very good fastness to light.

EXAMPLE 13

Detergent granules having a residual moisture of approx. 5% are prepared by spray-drying a slurry consisting of 1 part of water and 1 part of detergent of the following composition:

8.4 g of linear dodecylbenzenesulfonate, 3.1 g of tallow alcohol tetradecane ethylene glycol ether (14 EO), 3.7 g of Na soap (consisting mainly of behenic acid and $C_{14}$–$C_{20}$ acids), 45.8 g of Na tripolyphosphate, 7.9 g of Na silicate, 2.0 g of Mg silicate, 1.2 g of carboxymethylcellulose, 0.2 g of ethylenediamine tetraacetate, 22.2 g of Na sulfate and 0.8 g of the compound (2).

4 g of this detergent are dissolved in 1 l of water (12° of German hardness) at a temperature of 30° C. Five pieces of bleached cotton, each 10 g, are washed in this bath for 15 minutes at 30° C., then rinsed under cold, running water and centrifuged for 30 seconds in a swinging machine at a speed of revolution of approx. 1,000 r.p.m. This washing process is repeated 3 times and the pieces of cotton are then dried and their degree of whiteness is determined by the method of Ganz using a photometer (Zeiss RFC 3).

EXAMPLE 14

Detergents are prepared in accordance with Example 13, but containing 0.15 g of the compound (3) or 0.3 g of the compound (4) or 0.1 g of the compound (6), (9), (13) or (14) instead of the compound (2). The 3-fold washings are carried out as described in Example 13, but at a temperature of 90° C. The degrees of whiteness obtained are all above 145.

What is claimed is:

1. A process for the preparation of a compound of the formula (IIIa)

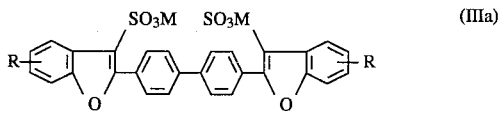

in which M is hydrogen and/or one equivalent of a non-chromophoric cation and R is one or more hydrogen, $C_1$–$C_4$alkyl, $C_1$–$C_4$alkoxy, halogen, phenoxy or benzyloxy radicals, which comprises reacting one mole of a compound of the formula (X)

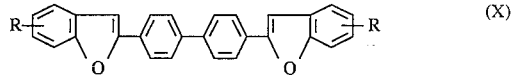

wherein R is as defined above, with at least a stoichiometric amount of an $SO_3$/base complex in an inert organic solvent, at a temperature of from 20° C. up to the boiling point of the solvent used.

2. A process according to claim 1, wherein M is sodium.

3. A process according to claim 1, which comprises reacting one mole of a compound of the formula (X)

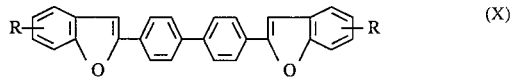

wherein each R is hydrogen or $C_1$–$C_4$alkyl with at least a stoichiometric amount of an $SO_3$/base complex in an inert organic solvent, at a temperature of from 20° C. up to the boiling point of the solvent used.

4. A process according to claim 3, wherein R is hydrogen.

5. A process according to claim 4, wherein the $SO_3$/base complex is a $SO_3$/pyridine complex.

6. A process according to claim 4, wherein the solvent is nitrobenzene.

* * * * *